United States Patent
Holmqvist (10) Patent No.: US 11,147,924 B2
(45) Date of Patent: *Oct. 19, 2021

(54) MEDICAMENT DELIVERY DEVICE AND METHOD OF ASSEMBLING THE SAME

(71) Applicant: SHL Medical AG, Zug (CH)

(72) Inventor: Anders Holmqvist, Varmdo (SE)

(73) Assignee: SHL MEDICAL AG, Zug (CH)

(*) Notice: Subject to any disclaimer, the term of this patent is extended or adjusted under 35 U.S.C. 154(b) by 203 days.

This patent is subject to a terminal disclaimer.

(21) Appl. No.: 16/373,099

(22) Filed: Apr. 2, 2019

(65) Prior Publication Data

US 2019/0240415 A1 Aug. 8, 2019

Related U.S. Application Data

(63) Continuation of application No. 14/774,877, filed as application No. PCT/EP2014/054563 on Mar. 10, 2014, now Pat. No. 10,272,203.

(30) Foreign Application Priority Data

Mar. 12, 2013 (SE) .................................... 1350291-9

(51) Int. Cl.
*A61M 5/315* (2006.01)
*A61M 5/32* (2006.01)
*A61M 5/31* (2006.01)

(52) U.S. Cl.
CPC ...... *A61M 5/31501* (2013.01); *A61M 5/3129* (2013.01); *A61M 5/3202* (2013.01);
(Continued)

(58) Field of Classification Search
CPC .... A61M 5/326; A61M 5/3202; A61M 5/321; A61M 2005/3247; A61M 2005/3267; A61M 5/3129; A61M 5/3267
See application file for complete search history.

(56) References Cited

U.S. PATENT DOCUMENTS

| 4,795,432 A | 1/1989 | Karczmer |
| 2007/0191809 A1 | 8/2007 | Westbye |

FOREIGN PATENT DOCUMENTS

| WO | 95/09022 A1 | 4/1995 |
| WO | 2006/080893 A1 | 8/2006 |

(Continued)

OTHER PUBLICATIONS

EPO, Int'l Search Report in PCT/EP2014/054563, dated Jun. 4, 2014.
EPO, Written Opinion in PCT/EP2014/054563, dated Jun. 4, 2014.

*Primary Examiner* — Tiffany Legette
(74) *Attorney, Agent, or Firm* — McDonnell Boehnen Hulbert & Berghoff LLP (57) ABSTRACT

Disclosed is an example device for injecting a medicament. The example device includes a housing having a distal end opening and a proximal end opening; a needle guard extending from the proximal end opening; an activation member extending from the distal end opening and movable relative to the housing from an initial position to a final position; and a final position lock disposed on an inner surface of the housing and configured to restrict movement of the activation member relative to the housing when the activation member is in the final position. An example method of assembling a device for injecting a medicament is also disclosed.

20 Claims, 10 Drawing Sheets

Related U.S. Application Data (60) Provisional application No. 61/777,389, filed on Mar. 12, 2013.

(52) U.S. Cl.
CPC ............ *A61M 5/326* (2013.01); *A61M 5/321* (2013.01); *A61M 2005/3247* (2013.01); *A61M 2005/3267* (2013.01); *A61M 2207/00* (2013.01)

(56) References Cited

FOREIGN PATENT DOCUMENTS

| | | |
|---|---|---|
| WO | 2012/000838 A2 | 1/2012 |
| WO | 2012/045350 A1 | 4/2012 |

MEDICAMENT DELIVERY DEVICE AND METHOD OF ASSEMBLING THE SAME

This application is a continuation of U.S. application Ser. No. 14/774,877, filed Sep. 11, 2015, which is a National Stage of International Application No. PCT/EP2014/054563, filed Mar. 10, 2014, which claims priority to Sweden Patent Application No. 1350291-9, filed Mar. 12, 2013, and U.S. Provisional Application No. 61/777,389, filed Mar. 12, 2013.

TECHNICAL FIELD

The present disclosure generally relates to a medical device and in particular to a disposable medicament delivery device and to a method of assembling such a device.

BACKGROUND

Parameters which normally are to be taken into account when designing disposable medicament delivery devices include measures to render it difficult to reuse the device and measures to protect users from needle sticks.

US2007/0191809 discloses a passive needle guard comprising a body, a shield covering the body and a spring disposed between the body and the shield. A needle can be mounted to the body at the proximal end thereof, i.e. at the end facing the user of the device during use. The body is arranged to receive a syringe for administration of a medicament. The spring biases the shield from the proximal end of the needle guard towards the distal end of the needle guard. A catch acts to retain the shield in the biased position. When the plunger reaches its final position, the thumb pad of the plunger releases the catch wherein the shield moves relative the body such that the proximal end of the body moves towards the distal end of the shield. The needle is thus received by the shield. The shield is locked in this position relative the body by means of a locking member which consists of a proximal end tab of the body engaging with an inner surface slot at the distal end of the shield.

A problem with existing solutions is however that the needle is not covered prior to administration of the medicament if the needle shield which normally covers the needle has been removed. Moreover, US2007/0191809 allows for the removal of the plunger post administration, which could render it possible to reuse the syringe.

SUMMARY

In view of the above, a general object of the present disclosure is to provide a medicament delivery device which at least mitigates the problems of the prior art.

Hence, according to a first aspect of the present disclosure there is provided a medicament delivery device for injection of a medicament, comprising: a housing having a distal end opening and a proximal end opening; a needle guard extending from the proximal end opening and moveable relative to the housing from an extended position to a retracted position in which the needle guard is biased towards the extended position; an activation member extending from the distal end opening and movable relative to the housing from an initial position to a final position; final position locking means arranged to restrict movement of the activation member relative to the housing when the activation member is in the final position; and needle guard locking means arranged to interact with the needle guard such that movement of the needle guard from the extended position to the retracted position is restricted when the activation member is in the final position.

The words "distal end" and "proximal end" may be used in conjunction with any of the components of the medicament delivery device. In each case, "proximal end" refers to that end of the component which is the end of component in the direction in which the needle points, and "distal end" refers to the opposite end.

An effect which may be obtainable hereby is that the needle guard, which is normally in the extended position relative the proximal end opening of the housing, covers the needle both prior to and after administration of a medicament. Prior to administration, the needle guard is movable between the extended position and the retracted position in which the needle guard is biased towards the extended position to protect the needle and to protect from needle sticks until administration of the medicament. After administration, i.e. when the activation member is in the final position, movement of the needle guard from the extended position is restricted. In this state, the needle guard covers the needle at all times and prevents needle stick and reuse of the medicament delivery device. The activation member is also restricted to move from its final position which provides additional protection from reuse of the medicament delivery device. It furthermore renders it more difficult to access the syringe after administration of the medicament.

According to one embodiment the activation member has a cutout and the housing has an inner surface provided with a final position locking member arranged to engage the cutout when the activation member is positioned in the final position.

Alternatively, the housing could comprise the cutout instead of the activation member and the activation member could be provided with the final position locking member instead of the housing for engagement with the cutout of the housing.

According to one embodiment the activation member has a blocking member arranged to prevent movement of the needle guard from the extended position to the retracted position when the activation member is in the final position. Thereby, axial movement of the needle guard towards the proximal end opening can be prevented.

According to one embodiment the needle guard has an activation member interaction leg which is aligned with and facing the blocking member when the activation member is in the final position and the needle guard is in the extended position.

According to one embodiment the housing has an inner surface provided with a blocking member pressing tab arranged to push the blocking member away from the inner surface when the activation member is in the final position to align the blocking member with the activation member interaction leg when the needle guard is in the extended position. Thereby, the blocking member can be positioned to prevent the activation member interaction leg, and thus the needle guard, to move towards the retracted position.

One embodiment comprises initial position locking means arranged to interact with the needle guard and with the actuation member such that movement of the activation member from the initial position to the final position is restricted when the needle guard is in the extended position. Hence, administration of the medicament is prevented as long as the needle guard is in the extended position. Administration of medicament is allowed only when the needle guard is set in the retracted position, i.e. when the medicament delivery device is in position to administer the medicament.

One embodiment comprises a container holder having a tab, wherein the initial position locking member comprises the tab, and wherein the activation member has a cutout, wherein the tab is arranged to engage the cutout in the initial position. The cutout of the activation member may according to one variation be the same cutout which is arranged to interact with the final position locking member of the housing.

According to one embodiment the needle guard has a container holder tab interaction leg arranged to push the tab out from the cutout when the needle guard is in the retracted position.

According to one embodiment the housing and the activation member have locking means arranged to interact such that movement of the activation member in a direction from the initial position to the final position is allowed, and movement of the activation member in the opposite direction is restricted.

According to one embodiment the final position locking member is a snap member.

According to one embodiment the tab of the container holder is a resilient snap moveable towards the container holder.

According to one embodiment the activation member is a manual plunger rod.

According to a second aspect of the present disclosure there is provided a method of assembling a medicament delivery device according to the first aspect. The method comprises: a) arranging a needle guard and a biasing member in a housing; b) arranging a drug cartridge in the housing; and c) arranging, via a distal end opening of the housing, the activation member in the housing.

One embodiment comprises arranging a container holder in the housing, wherein the drug cartridge is arranged in the container holder.

According to one embodiment the needle guard is arranged in the housing from any of the distal end opening and a proximal end opening of the housing.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

Figure 1:
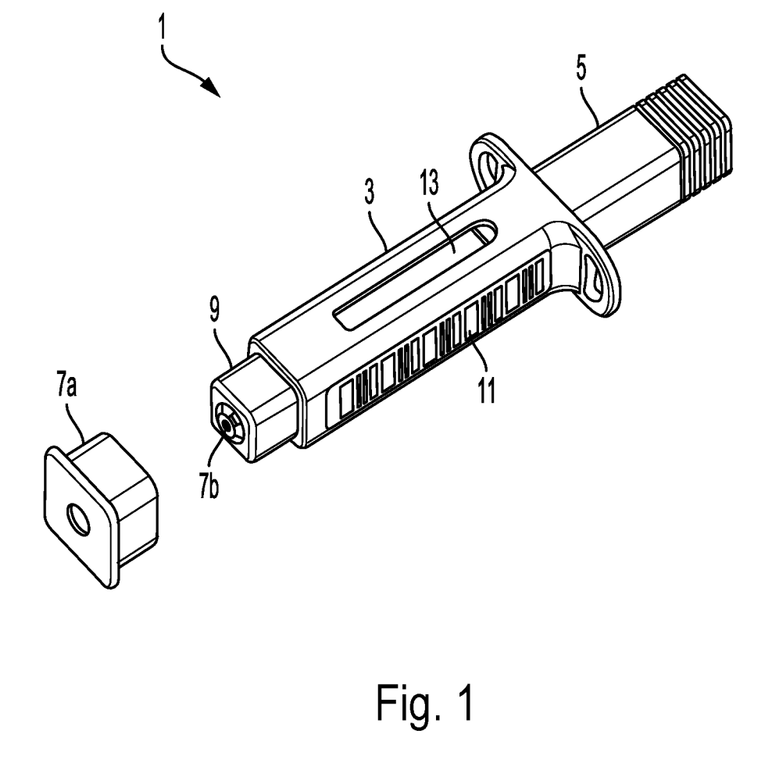
FIG. 1 is a perspective view of an example of a medicament delivery device.

FIG. 1 depicts an example of a medicament delivery device 1 loaded with a syringe containing a drug and ready for use. The medicament delivery device 1 comprises a housing 3, an activation member 5, a cap 7a, a syringe needle shield 7b, a needle guard 9, and a label 11 with information of the drug contained in the medicament delivery device 1. The label 11 can for example be provided on an external surface of the housing 3. The housing 3 may further have a transparent window 13 which allows inspection of the drug prior to the administration thereof.

The housing 3 has a proximal end opening 3a, a distal end opening 3b opposite the proximal end opening 3a and a through opening extending from the proximal end opening 3a to the distal end opening 3b. The activation member 5 is coaxially arranged in the housing 3 and extends from the housing 3 at the distal end thereof through the distal end opening 3b. The activation member 5 is moveable relative to the housing 3 from an initial position to a final position.

The activation member 5 is sleeve shaped and has a predetermined length depending on the volume of medicament contained within the syringe. The activation member comprises an open and closed end In FIG. 1, the activation member is in an initial position relative to the housing 3. The initial position is the position in which the activation member 5 is arranged prior to the injection of a drug, i.e. the position in which the activation member protrudes a predetermined length from the distal end opening 3b of the housing and wherein said predetermined length may correspond to the stroke length for delivering the complete volume of medicament within the syringe. The activation member 5 is in a final position when a maximal allowed portion of the activation member 5 has been received by the housing 3, as will be illustrated in FIGS. 7-9. The activation member 5 is in the final position when the drug has been fully administered, i.e. in the position in which the predetermined length of the activation member is positioned within the housing.

The medicament delivery device 1 further comprises final position locking means which are arranged to restrict movement of the activation member 5 relative to the housing 3 when the activation member 5 is in the final position. In the following, the final position locking means will be exemplified by a final position locking member 3g of the housing, as shown in FIG. 3b, and a corresponding cutout 5b in the activation member 5. The medicament delivery device 1 also comprises needle guard locking means arranged to interact with the needle guard such that movement of the needle guard 9 from an extended position to a retracted position is restricted when the activation member 5 is in the final position. In the following, the needle guard locking means will be exemplified by a blocking member 5a of the activation member 5 and a blocking member pressing tab 3h, as shown in FIG. 3b, on the inner surface of the housing 3.

Figure 2:
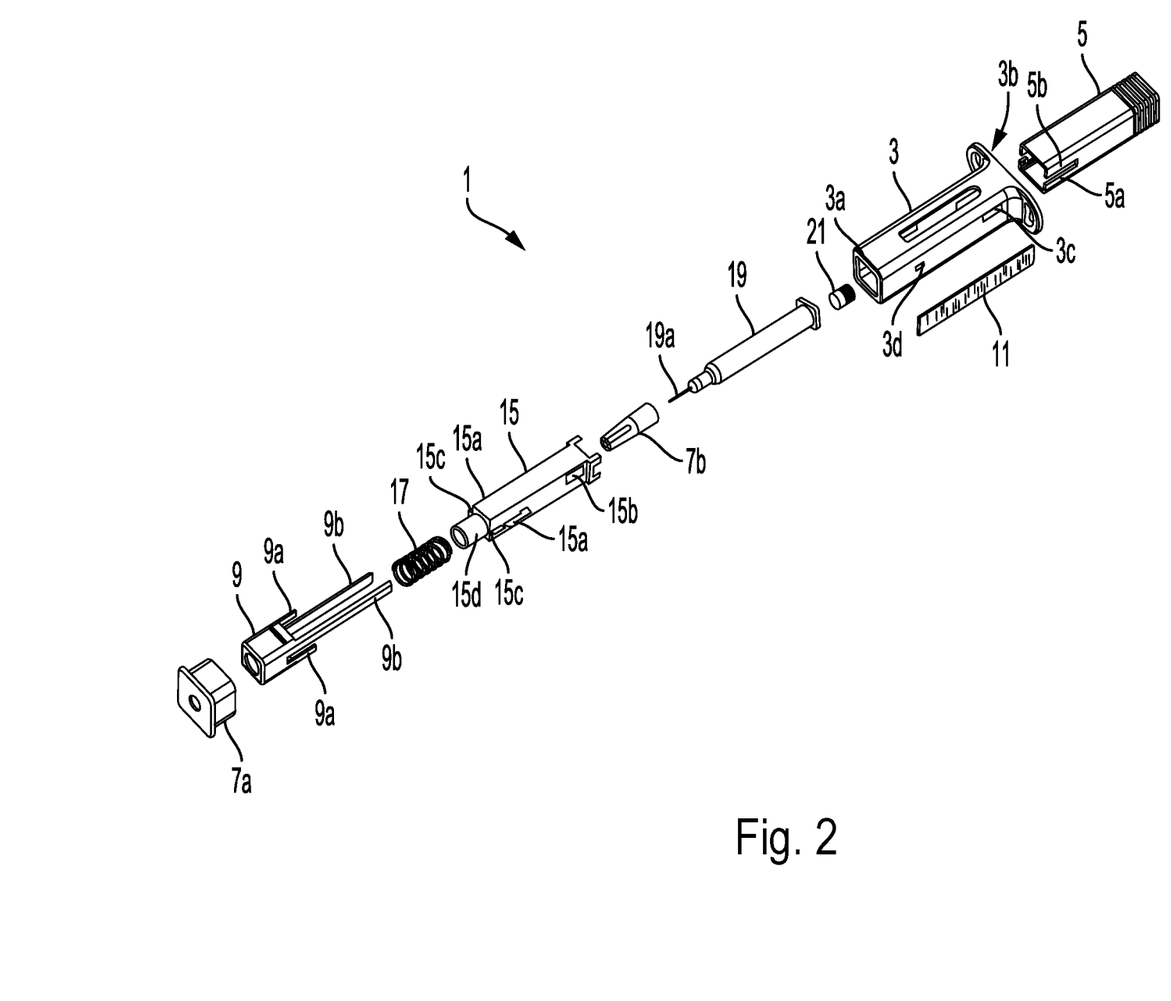
FIG. 2 is an exploded view of the medicament delivery device in FIG. 1.

FIG. 2 is an exploded view of the medicament delivery device 1. In addition to the components shown in FIG. 1, the exemplified medicament delivery device 1 comprises a container holder 15 i.e. a syringe holder, a spring 17, a drug syringe 19 having a needle and a stopper 21.

The needle guard 9 is coaxially arranged in the housing 3 and extends from the housing 3 at the proximal end thereof through the proximal end opening 3a. The needle guard 9 is moveable relative to the housing 3 from the extended position to the retracted position in which the needle guard is biased towards the extended position by means of a biasing member, which in the present example is the spring 17. The activation member 5 and the needle guard 9 extend in opposite directions from the housing 3. The activation member 5 has a larger cross-sectional dimension than the needle guard 9, allowing the distal end portions of the needle guard to move within the activation member 5.

The housing 3 and the activation member 5 have locking means arranged to interact such that movement of the activation member 5 in a direction from the initial position to the final position is allowed, and movement of the activation member in the opposite direction is restricted. According to the present example, the locking means of the housing 3 is defined by a blocking member 3c and the corresponding locking means of the activation member 5 is defined by a cutout 5b. The blocking member 3c of the housing 3 hence prevents the removal of the activation member 5 from the housing 3. It is envisaged that as an alternative hereto the housing could be provided with the cutout and the activation member could comprise the blocking member.

The exemplified housing 3 has a cutout 3d at a side thereof. The cutout 3d locks or fixes the housing 3 to the container holder 15 which has a corresponding lateral leg 15a which engages the cutout 3d. There may be several cutouts 3d along the periphery of the housing 3 with corresponding lateral legs 15a protruding from the container holder 15. It should be noted that instead of the lateral leg 15a engaging the cutout 3d and thus fixing the container holder 15 to the housing 3, the end portions of the lateral legs could be integrated with the housing so as to form a single piece housing and container holder. In this case, the end portions of the lateral legs could for example be moulded to the inner surface of the housing during manufacturing, thus integrating the housing and the container holder.

The needle guard 9 is in the extended position relative to the housing 3. The extended position is the position in which the needle guard protrudes a predetermined length from the proximal end opening 3a of the housing and wherein said predetermined length may correspond to the length for covering the needle from sight. The needle guard 9 is in a retracted position when a maximal allowed portion of the needle guard 9 has been received by the housing 3, as will be illustrated in FIGS. 7-8. The needle guard 9 is in the retracted position when the needle is exposed to sight.

The activation member 5 comprises a blocking member 5a at the proximal end thereof. According to the example in FIG. 2, the blocking member 5a is a resilient leg extending at the proximal end of the activation member 5. The blocking member 5a is arranged to prevent movement of the needle guard 9 from the extended position to the retracted position when the activation member 5 is in the final position. The activation member 5 further has a cutout 5b which is open in a direction facing the blocking member 5a, i.e. the resilient leg. The cutout 5b has three functions according to the present example. The first function of the cutout 5b is to fix the activation member 5 in the initial position via interaction with an initial position locking member of the container holder 15 when the needle guard 9 is in the extended position. The second function of the cutout 5b is to fix the activation member 5 in the final position via interaction with a final position locking member of the housing 3, as will be described in more detail with reference to FIGS. 3a-b. The third function of the cutout 5b is to interact with the blocking member 3c of the housing to prevent removal of the activation member 5 from the housing 3.

The syringe 19, which contains the drug to be administered or injected, comprises a needle 19a. Upon assembly, the syringe 19 is arranged in the container holder 15 which is hollow. The needle shield 7b, which may be a flexible needle shield (FNS) or a rigid needle shield (RNS), is arranged to receive the needle 19a to protect the needle. The cap 7a can be arranged on the needle guard 9 to cover the needle guard 9 and thereby provide robust protection of the needle 19a for example during transport and storage of the medicament delivery device 1. The needle shield 7b can be arranged to cover the needle 19a. In particular, the needle shield 7b can be fixedly attached to the inside of the cap 7a in such a manner that the needle shield 7b is removed simultaneously with the cap 7a.

The container holder 15 further has initial position locking means 15b arranged to interact with the needle guard 9 and with the actuation member 5 such that movement of the activation member 5 from the initial position to the final position is restricted when the needle guard 9 is in the extended position. According to the present example the initial position locking means 15b comprises a tab arranged to engage the cutout 5b of the activation member 5 when the activation member 5 is in the initial position, fixing the activation member 5 in the initial position until the needle guard 9 is moved to the retracted position. The initial position locking means 15b or tab of the container holder 15 is a resilient snap moveable towards the container holder 15. The initial position locking means 15b may extend in an inclined manner in a direction from the proximal end to the distal end of the container holder 15.

The container holder 15 has a proximal end portion 15d around which the spring 17 is arranged. When the medicament delivery device 1 is assembled, the spring 17 is arranged between the needle guard 9 and the container holder 15. The spring 17 is tensioned when the needle guard 9 is in the retracted position. In the retracted position the needle guard is thus biased towards the extended position.

The needle guard 9 has an activation member interaction leg 9a. The activation member interaction leg 9a is aligned with and facing the blocking member 5a of the activation member 5 when the activation member 5 is in the final position and the needle guard 9 is in the extended position, i.e. after injection when the needle 19a has been pulled out from the skin. The needle guard 9 further has a container holder tab interaction leg 9b adapted to push the initial position locking member 15b, i.e. the tab, out from the cutout 5b of the activation member 5 when the needle guard 9 is in the retracted position. The container holder tab interaction leg 9b extends towards the cutout 5b of the activation member 5 and is aligned with the cutout 5b and the initial position locking member 15b.

Figure 3A:
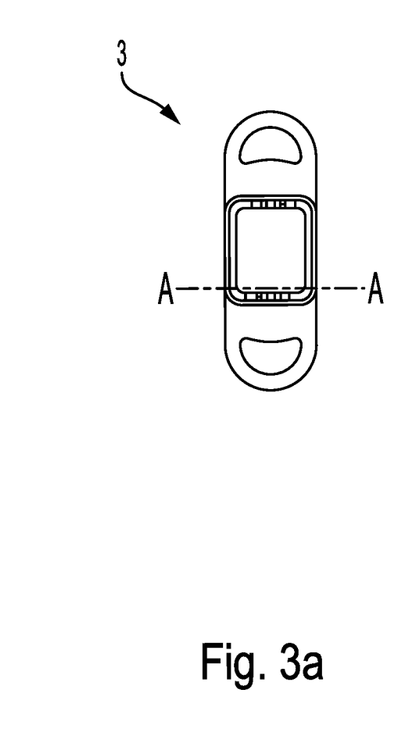
FIGS. 3a-b is a top view and a longitudinal section, respectively, of a housing of the medicament delivery device in FIG. 1.
Figure 3B:
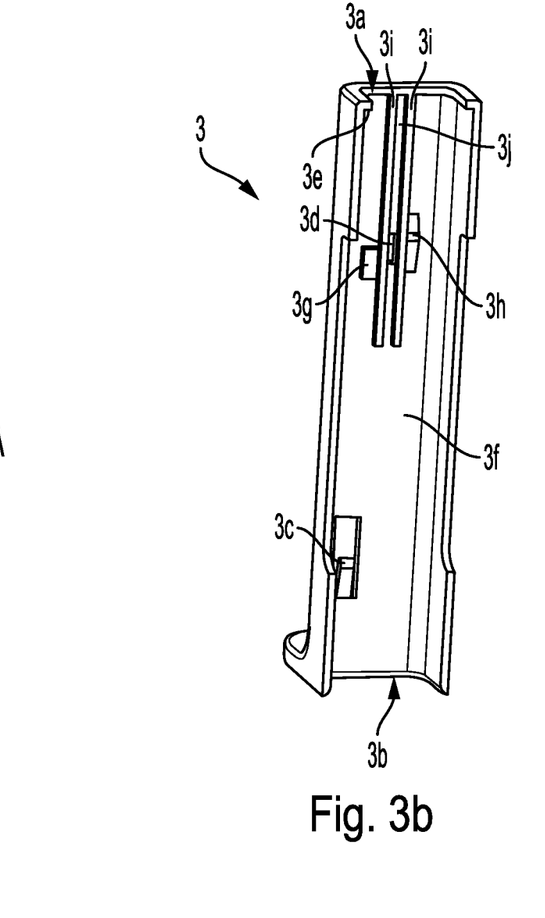

FIG. 3a is a top view of the housing 3 showing its distal end, and FIG. 3b is a longitudinal section of the housing 3 along lines A-A. In FIG. 3b, a perspective view of a portion of the interior of the housing 3 is shown. The proximal end opening 3a has a rim 3e which retains the needle guard 9 in the housing 3. In particular, the rim 3e abuts a shoulder 9c, shown in FIG. 4, of the needle guard 9 when the needle guard 9 is in the extended position. The housing 3 has an inner surface 3f provided with a final position locking member 3g aligned with the cutout 5b of the activation member 5 in a direction from the distal end to the proximal end of the housing 3. The final position locking member 3g is arranged to interact with the actuation member 5 such that movement of the activation member 5 is restricted when positioned in the final position. In particular, the final position locking member 3g may comprise or be defined by a tab or snap member. The tab or snap member is according to one example wedge-shaped, wherein the tab or snap member has an inclined face forming a ramp in the direction from the distal end to the proximal end of the housing 3. From the other direction, i.e. from the proximal end to the distal end, the face adjacent the ramp face may be essentially perpendicular to the internal surface 3f. The final position locking member 3g engages with the cutout 5b of the activation member 5 when the activation member 5 is in the final position. The final position locking member 3g may hence efficiently prevent movement of the activation member 5 once it has reached its final position.

The inner surface 3f is further provided with a blocking member pressing tab 3h protruding from the inner surface 3f. The blocking member pressing tab 3h is aligned with the blocking member 5a in a direction from the distal end to the proximal end of the housing 3. The blocking member pressing tab 3h is arranged to press the blocking member 5a, i.e. the resilient leg, of the activation member 5 away from the inner surface 3f when the activation member 5 is in the final position. When the needle guard 9 is in the retracted position, the blocking member 5a is pushed against the outer surface of the activation member interaction leg 9a because the cross-sectional dimension of the needle guard 9 is smaller than the cross-sectional dimension of the activation member 5. When the needle guard 9 is moved to the extended position the activation member interaction leg 9a is retracted from below the blocking member 5a. The blocking member 5a is therefore pushed further away from the inner surface 3f of the housing by the blocking member pressing tab 3h until the blocking member 5a is in level with the path of movement of the activation member interaction leg 9a. In this position, the tip of the blocking member 5a is aligned with and faces the tip of the activation member interaction leg 9a. Hence axial movement of the activation member interaction leg 9a is restricted when the needle guard 9 is in the extended position combined with the activation member 5 being in the final position.

The container holder 15 has lateral guiding elements 15c which are arranged to interact with corresponding guiding elements 3i in the housing 3. The guiding elements 15c of the container holder 15 could be protruding tabs or slits, depending on the design of the corresponding guiding elements 3i in the housing 3. According to the present example, the inner surface 3f of the housing 3 is provided with guiding elements 3i which interact with the lateral guiding elements 15c of the container holder 15. Alignment of the housing 3 and the container holder 15 may thereby be obtained in a simple manner when assembling the medicament delivery device 1. Especially, the guiding elements 3i and 15c guide the lateral legs 15a to the cutouts 3d of the housing 3 for attachment of the housing 3 to the container holder 15.

Figure 4:
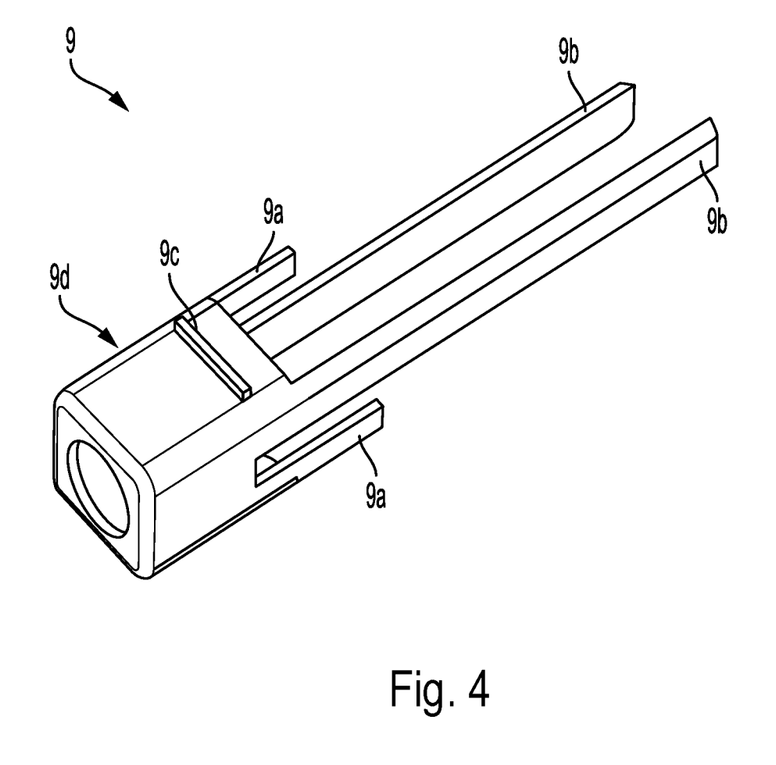
FIG. 4 is a perspective view of a needle guard of the medicament delivery device in FIG. 1.

FIG. 4 is a perspective view of the needle guard 9. The needle guard 9 has a main body 9d which is arranged to house the needle 19a when the needle guard 9 is in the extended position. The activation member interaction legs 9a extend distally from the main body 9d. The container holder tab interaction legs 9b extend distally from the needle guard 9 towards the activation member 5. The container holder tab interaction legs 9b have a longer longitudinal extension than the activation member interaction legs 9a. The main body 9 is provided with a shoulder 9c. The shoulder 9c can for example have a rectangular cross-section or a triangular cross-section. The shoulder 9c may thus for example be chamfered, defining a ramp in a direction from the distal end to the proximal end. Depending on the shape of the shoulder 9c, arrangement of the needle guide 9 into the housing 3 may either be performed from the distal end opening 3b or the proximal end opening 3a of the housing 3 during assembly of the medicament delivery device 1.

Figure 5:
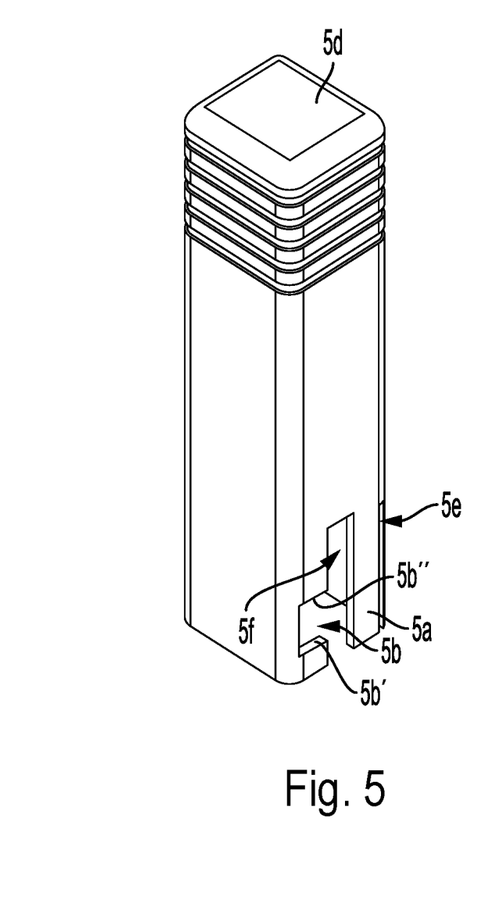
FIG. 5 is a perspective view of an activation member of the medicament delivery device in FIG. 1.

FIG. 5 is a perspective view of the activation member 5. The activation member 5 is preferably a manual rod. The activation member 5 has an open proximal end and a distal end 5d which is closed. The cutout 5b, which may be open or closed, has a proximal edge 5b' and a distal edge 5b" opposite the proximal edge 5b'. The proximal edge 5b' interacts with the final position locking member 3g in the final state. For example, the final position locking member 3g of the housing 3, and in particular the face adjacent the ramp face, may abut the proximal edge 5b' when the activation member 5 is in the final position. The proximal edge 5b' also interacts with the blocking member 3c of the housing 3 in the initial position to prevent the activation member 5 to be removed from the housing 3. The distal edge 5b" interacts with the initial position locking means 15b in the initial state preventing the activation member 5 to be moved to the final state when the needle guard 9 is in the extended position. The exemplified activation member 5 has a through slit 5e and through opening 5f on respective sides of the blocking member 5a defining a leg and thereby rendering the blocking member 5a resilient. According to the present example, the cutout 5b forms part of the through opening 5f. It is however to be noted that the cutout could alternatively be an isolated through opening.

The activation member 5 may have a hollow interior comprising a plunger rod extending longitudinally from the distal end 5d to the proximal end inside the activation member 5. The plunger rod may be arranged in a distal end opening of the syringe 19 and the syringe may be sealed by means of the stopper 21. Movement of the activation member 5 from the initial position to the final position hence moves the plunger rod in the syringe and allows for injection of the drug. Alternatively, the plunger rod could be a component that separate from the activation member and forming part of the syringe. In this case, the activation member could have a hollow interior allowing the reception of the plunger rod for enabling manoeuvring of the plunger rod.

Figure 6A:
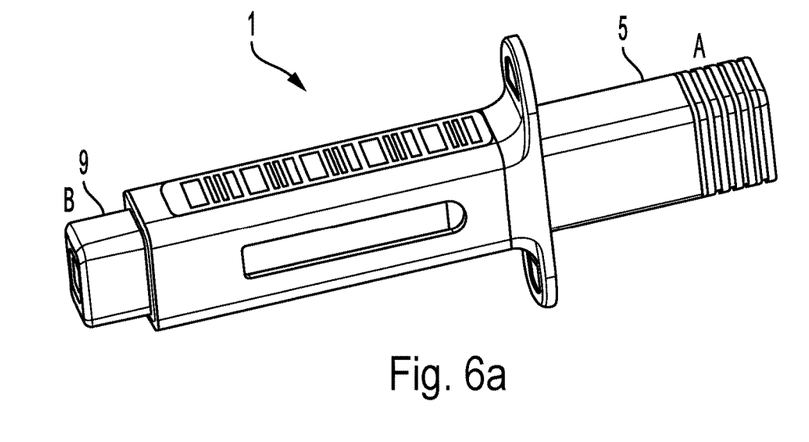
FIGS. 6a-b are perspective views of a medicament delivery device in an initial state.

The functioning of the medicament delivery device 1 will now be described in more detail with reference to FIGS. 6-9. FIG. 6a is a perspective view of the medicament delivery device 1 in a default state, which is the state of the device 1 wherein the cap 7a together with the needle shield 7b has been removed from the device.

The medicament delivery device 1 is loaded with a syringe containing a drug and is ready for use. The activation member 5 is in the initial position A. The needle guard 9 is in the extended position B. Thus, movement of the activation member 5 towards the final position is restricted.

Figure 6B:
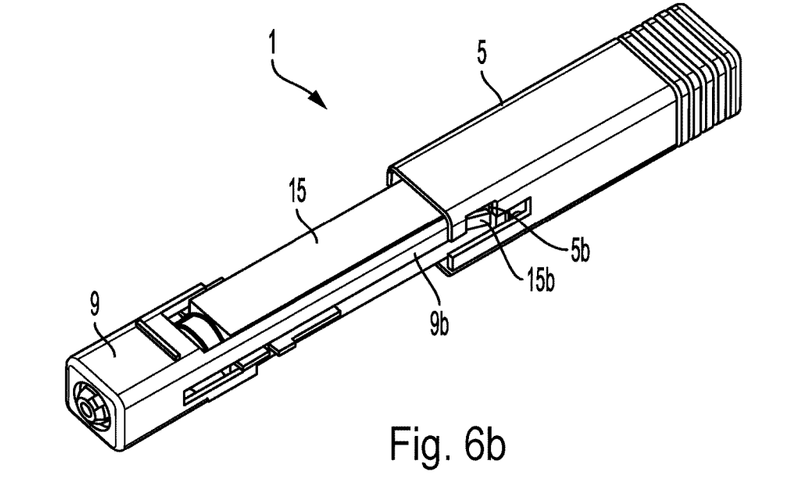

FIG. 6b shows the medicament delivery device 1 with the housing removed to make visible internal components in the default state. It can be seen that the initial position locking means 15b, a snap member, extends into the cutout 5b of the activation member 5 to restrict movement of the activation member 5 towards the final position. The container holder tab interaction leg 9b of the needle guard 9 is aligned with the initial position locking means 15b. The container holder tab interaction leg 9b extends from the main body 9d of the needle guard 9 towards the initial position locking means 15b which protrudes from the container holder 15 in an inclined manner in a direction from the proximal end to the distal end of the container holder 15 into the cutout 5b.

Figure 7A:
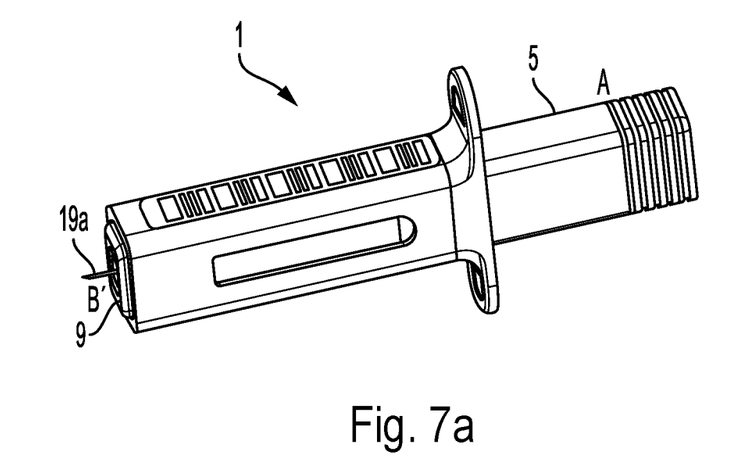
FIGS. 7a-b are perspective views of a medicament delivery device in an inserted state.

FIG. 7a is a perspective view of medicament delivery device 1 in a state in which the needle 19a normally is inserted into an object such as a patient for administration of the drug. In this state, the needle guard 9 is in the retracted state B', in which the needle 19a is emerged. The activation member 5 is still in the initial state A. The drug is at this point thus still fully contained in the syringe.

Figure 7B:
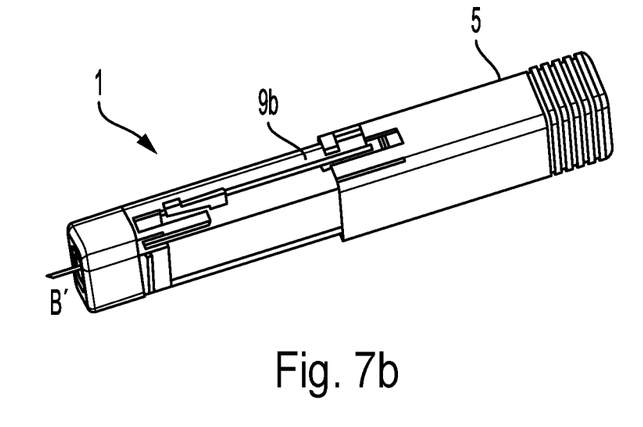

FIG. 7b shows the medicament delivery device 1 with the housing removed to make visible internal components in the state shown in FIG. 7a. As can be seen, by means of the movement of the needle guard 9 from the extended position B to the retracted position B', the container holder tab interaction leg 9b has moved in a direction from the proximal end to the distal end. By this movement, the initial position locking member 15b, which is resilient and in its normal state inclined in a direction from the proximal end to the distal end, has been pushed underneath the container holder tab interaction leg 9b of the needle guard 9. Hereby, the activation member 5 is released in the sense that it may now be moved from the initial position A to the final position A', as shown in FIG. 8a.

Figure 8A:
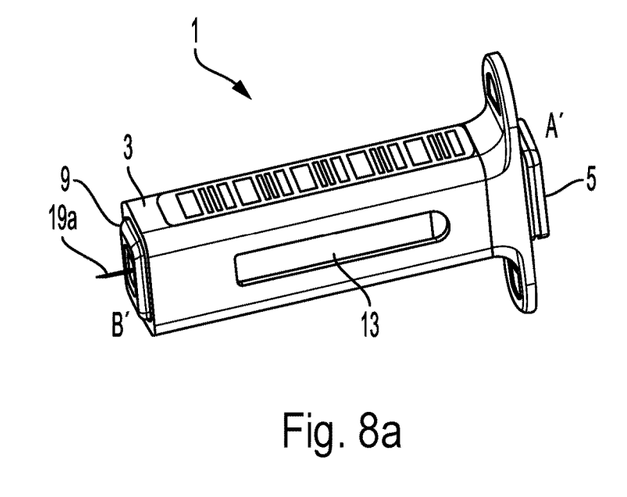
FIGS. 8a-b are perspective views of a medicament delivery device in an state when a drug injection has been performed.

FIG. 8a is perspective view of medicament delivery device 1 in a state when injection has been finalised but the needle 19a is still inserted in the patient. The needle guard 9 is in the retracted position B' and the activation member 5 is in the final position A'. It can be noted that the transparent window 13 is covered by the activation member 5.

Figure 8B:
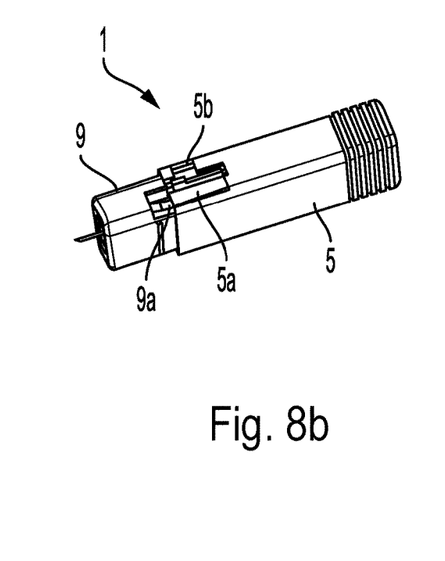

FIG. 8b shows the medicament delivery device 1 with the housing removed to make visible internal components in the state shown in FIG. 8a. Although the housing 3 is removed, it can be seen that the blocking member 5a of the activation member is pushed away from the inner surface of the housing inwards in the medicament delivery device 1. The blocking member 5a is pushed inwards by the blocking member pressing tab 3h, not shown in FIG. 8b. The blocking member 5a rests on the activation member interaction leg 9a of the needle guard 9. The final position locking member 3g, also not shown, of the housing 3 engages with the cutout 5b in the final position, restricting the movement of the activation member 5.

Figure 9A:
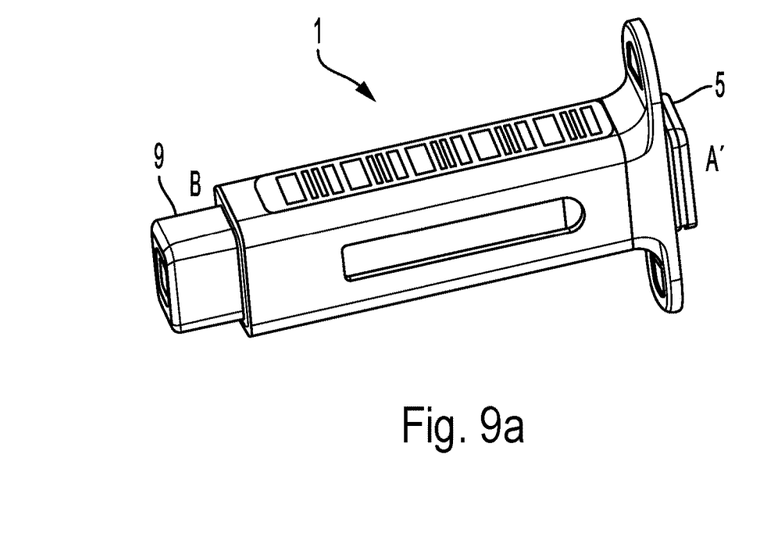
FIGS. 9a-b show a medicament delivery device in a pulled out state.

FIG. 9a is perspective view of medicament delivery device 1 in its final state when it has been pulled out from the patient. In this state the needle guard 9 is again in the extended position B, which is obtained due to the biasing force of the spring 17. The activation member 5 is in the final position A'.

Figure 9B:
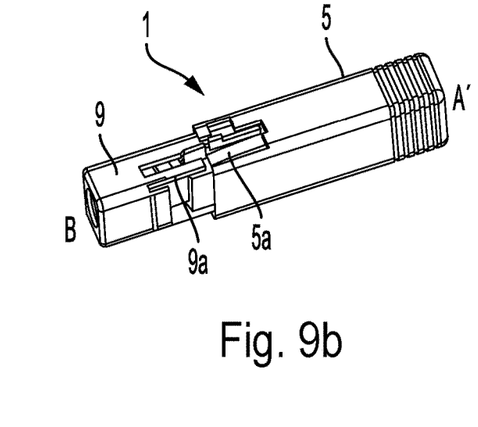

FIG. 9b shows the medicament delivery device 1 with the housing removed to make visible internal components in the final state. Just as in FIGS. 8a-b, the final position locking member of the housing engages with the cutout 5b in the final position, restricting the movement of the activation member 5. Since the needle guard 9 has a smaller cross-sectional dimension than the activation member 5, the needle guard 9 would be allowed to move to the retraced position B' if the blocking member 5a was not pushed in a direction away from the inner surface of the housing. The blocking member 5a is however pushed inwards by the blocking member pressing tab 3h of the housing, blocking movement of the activation member interaction leg 9a thus restricting axial movement of the needle guard 9. The movement of the needle guard 9 is hence restricted when the activation member 5 is in the final position A'.

Figure 10:
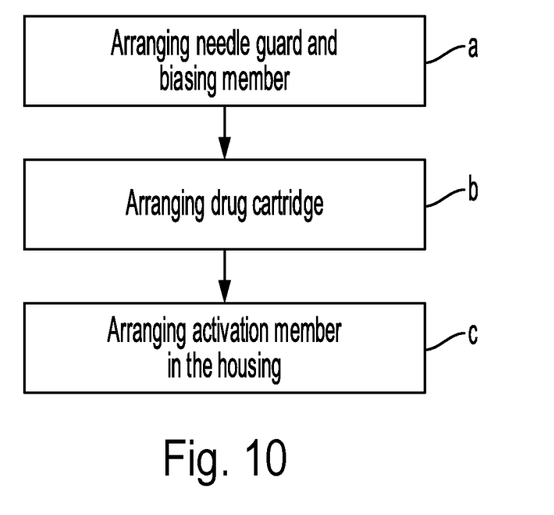
FIG. 10 is a flowchart describing a method of assembling the medicament delivery device in FIG. 1.

FIG. 10 is a flowchart of a method of assembling a medicament delivery device such as medicament delivery device 1. In a step a) the needle guard 9 and a biasing member are arranged in the housing 3. The biasing member may for example be a spring 17. The needle guard 9 and the biasing member may be placed in the housing 3 from either the proximal end opening 3a or the distal end opening 3b. If the shoulder 9c is chamfered as described above, the needle guard 9 may be inserted into the housing 3 from the proximal end opening 3a. Otherwise, the needle guard 9 is inserted into the housing through the distal end opening 3b. In a step b) a drug cartridge, i.e. a syringe, is arranged in the housing 3. The syringe is typically inserted from the distal end opening 3b of the housing 3. In a step c) the activation member 5 is arranged in the housing 3. The activation member 5 is inserted into the housing 3 from the distal end opening 3b of the housing 3.

If the housing 3 and the container holder 15 are separate components, the container holder is inserted into the housing prior to step b). If the housing and the container holder are an integrated unit, the syringe is placed in the integrated housing and container holder. The label 11 can be arranged on the housing 3 before or after assembly of the medicament delivery device.

The medicament delivery device presented herein hence protects users from needle sticks prior to and after administering a drug. The needle essentially only appears during the operation of injection of the drug. Moreover, the activation member and the needle guard are fixed relative the housing after administration of the drug, rendering reuse of the medicament delivery device difficult. The medicament delivery device may for example be used for drug administration for the treatment of diabetes, rheumatism, or to treat growth hormone deficiency in children. The medicament delivery device may for example be manufactured of plastic.

The inventive concept has mainly been described above with reference to a few examples. However, as is readily appreciated by a person skilled in the art, other embodiments than the ones disclosed above are equally possible within the scope of the inventive concept, as defined by the appended claims. For example, instead of the final position locking means being comprised of a final position locking member 3g of the housing and a corresponding cutout 5b in the activation member 5, the housing could be provided with a cutout and the activation member could be provided with a final position locking member, e.g. a snap. In this case, the cross-sectional dimension of the needle guard could be larger than that of the activation member so that the activation member could partially be received by the needle guard. The initial position locking means could be a resilient snap provided on the external surface of the activation member and distal leg of the needle guard could be arranged to interact with the initial position locking means to allow movement of the activation member when the needle guard is in the retracted position. The needle guard locking means could be a snap member extending from the container holder pushing the blocking member, e.g. a resilient leg, of the activation member towards the inner surface of the housing, thus blocking the movement path of a corresponding leg of the needle guard. Alternatively, the housing could instead of a blocking member pressing tab be provided with a slot which extends along the inner surface of the housing from the distal end to the location of the tab according to the detailed example described hereabove and the blocking member of the activation member could be provided with a tab slideably arranged in the slot thus pushing the blocking member away from the housing when the activation member is in the final position.

The invention claimed is:

1. A device for injecting a medicament, comprising:
a housing having a distal end opening and a proximal end opening; a needle guard extending from the proximal end opening;
an activation member rotationally fixed relative to the housing and slidably positioned within the housing such that a first portion of an outer surface of the activation member extends longitudinally from an inside surface of the distal end opening when the activation member is in an initial position, where during injection of the medicament the activation member is moved axially relative to the housing in a proximal direction to a final position such that a second portion of the outer surface extends longitudinally from the distal end opening, where the second portion is smaller than the first portion; and
a final position lock disposed on an inner surface of the housing and configured to restrict movement of the activation member relative to the housing when the activation member is in the final position.

2. The device of claim 1, wherein the activation member has an edge, and the final position lock engages the edge when the activation member is in the final position.

3. The device of claim 1, wherein the final position lock is a snap member.

4. The device of claim 1, wherein the activation member is a manual plunger rod.

5. The device of claim 1, wherein the housing and the activation member have interacting locks that allow movement of the activation member in a direction from the initial position to the final position and restrict movement of the activation member in an opposite direction.

6. The device of claim 1 further comprising a needle guard lock configured to interact with the needle guard such that movement of the needle guard is restricted when the activation member is in the final position.

7. The device of claim 1, wherein the activation member has a blocking member configured to prevent movement of the needle guard when the activation member is in the final position and the needle guard is in an extended position relative to the housing.

8. The device of claim 7, wherein the needle guard has an activation member interaction leg that is aligned with and faces the blocking member when the activation member is in the final position the needle guard is in the extended position.

9. The device of claim 1, further comprising an initial position lock configured to interact with the activation member such that movement of the activation member from the initial position to the final position is restricted when the needle guard is in an extended position relative to the housing.

10. The device of claim 9, further comprising a container holder, wherein the initial position lock comprises a tab on the container holder, the activation member has an edge, and the tab is configured to engage the edge in the initial position.

11. The device of claim 10, wherein the tab on the container holder is a resilient snap movable toward the container holder.

12. The device of claim 10, wherein the container holder is arranged in the housing and is configured to hold a medicament cartridge.

13. A method of assembling a device for injecting a medicament, the method comprising:
arranging a needle guard in a housing of the device, wherein the housing has a distal end opening and a proximal end opening, wherein the needle guard is arranged such that the needle guard extends from the proximal end opening; and
arranging, via the distal end opening of the housing, an activation member in the housing such that the activation member is rotationally fixed relative to the housing and slidably positioned within the housing such that a first portion of an outer surface of the activation member extends longitudinally from an inside surface of the distal end opening when the activation member is in an initial position, where during injection of the medicament the activation member is moved axially relative to the housing in a proximal direction to a final position such that a second portion of the outer surface extends longitudinally from the distal end opening and where the second portion is smaller than the first portion,
wherein a final position lock is disposed on an inner surface of the housing and configured to restrict movement of the activation member relative to the housing when the activation member is in the final position.

14. The method of claim 13, wherein arranging the needle guard in the housing comprises arranging the needle guard in the housing from the distal end opening of the housing or the proximal end opening of the housing.

15. The method of claim 13, wherein the activation member has an edge, and the final position lock engages the edge when the activation member is in the final position.

16. The method of claim 13, wherein the final position lock is a snap member and the activation member is a manual plunger rod.

17. The method of claim 13, further comprising arranging a container holder in the housing, wherein the container holder is configured to hold a medicament cartridge.

18. The method of claim 17, wherein a tab is on the container holder, the activation member has an edge, and the tab is configured to engage the edge in the initial position such that movement of the activation member from the initial position to the final position is restricted when the needle guard is in an extended position relative to the housing.

19. The method of claim 13, wherein the activation member has a blocking member configured to prevent movement of the needle guard when the activation member is in the final position and the needle guard is in an extended position relative to the housing.

20. The method of claim 19, wherein the needle guard has an activation member interaction leg that is aligned with and faces the blocking member when the activation member is in the final position and the needle guard is in the extended position.

* * * * *